(12) United States Patent
Fenn et al.

(10) Patent No.: US 9,339,263 B2
(45) Date of Patent: May 17, 2016

(54) DILATION SYSTEM AND METHOD

(71) Applicant: DEPUY SYNTHES PRODUCTS, INC., Raynham, MA (US)

(72) Inventors: Matt Fenn, Raynham, MA (US); Sean Saidha, Raynham, MA (US); Henry Rutledge, Lansdale, PA (US); Zoher Bootwala, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 142 days.

(21) Appl. No.: 14/147,345

(22) Filed: Jan. 3, 2014

(65) Prior Publication Data
US 2015/0190128 A1 Jul. 9, 2015

(51) Int. Cl.
| | | |
|---|---|---|
| *A61B 17/00* | (2006.01) | |
| *A61B 17/02* | (2006.01) | |
| *A61B 1/018* | (2006.01) | |
| *A61B 1/32* | (2006.01) | |
| *A61B 5/00* | (2006.01) | |
| *A61B 17/34* | (2006.01) | |
| *A61B 5/04* | (2006.01) | |
| *A61M 29/00* | (2006.01) | |

(52) U.S. Cl.
CPC ............. *A61B 17/0218* (2013.01); *A61B 1/018* (2013.01); *A61B 1/32* (2013.01); *A61B 5/4836* (2013.01); *A61B 5/4893* (2013.01); *A61B 17/0293* (2013.01); *A61B 17/3421* (2013.01); *A61B 17/3423* (2013.01); *A61B 17/3468* (2013.01); *A61B 5/04001* (2013.01); *A61B 2017/00039* (2013.01); *A61B 2017/3433* (2013.01); *A61M 29/00* (2013.01)

(58) Field of Classification Search
CPC ........................ A61B 5/04001; A61B 17/0218
USPC .................. 606/190–191; 600/201, 205, 234, 600/210–217; 607/117
See application file for complete search history.

(56) References Cited

U.S. PATENT DOCUMENTS

| | | | | |
|---|---|---|---|---|
| 5,782,807 A * | 7/1998 | Falvai | ............... | A61M 25/0097 604/164.1 |
| 7,618,431 B2 * | 11/2009 | Roehm, III | ........ | A61B 17/1757 600/210 |
| 7,879,009 B1 * | 2/2011 | Haddock | .................. | A61B 1/32 600/210 |
| 8,000,782 B2 * | 8/2011 | Gharib | ................. | A61B 5/0492 600/546 |
| 8,075,581 B2 * | 12/2011 | Thramann | ............... | A61B 17/58 600/201 |
| 8,340,779 B2 * | 12/2012 | Harris | ................ | A61B 17/3401 600/549 |
| 8,608,652 B2 * | 12/2013 | Voegele | ................. | A61B 1/303 600/207 |
| 8,852,242 B2 * | 10/2014 | Morgenstern Lopez | ................ | A61B 17/1757 606/279 |
| 8,852,243 B2 * | 10/2014 | Morgenstern Lopez | ................ | A61B 17/1757 606/279 |
| 8,876,851 B1 * | 11/2014 | Woolley | ................ | A61M 29/00 606/198 |
| 8,998,803 B2 * | 4/2015 | Hanes, II | ........... | A61B 17/0218 600/184 |
| 9,028,522 B1 * | 5/2015 | Prado | ................... | A61B 17/025 606/191 |
| 2002/0022873 A1* | 2/2002 | Erickson | ............. | A61B 5/0422 607/117 |

(Continued)

*Primary Examiner* — Ellen C Hammond
*Assistant Examiner* — Staurt S Bray
(74) *Attorney, Agent, or Firm* — Dunlap Codding, P.C.

(57) ABSTRACT

A dilator system includes a series of sequential dilators. A first dilator has an elongated body having a major axis and a minor axis, the minor axis being substantially normal to the major axis. A second dilator has an elongated body having a major axis and a minor axis, the minor axis of the second dilator being substantially normal to the major axis of the second dilator. A bore of the second dilator is configured to matingly receive the first dilator in such a way that the major axis of the second dilator is aligned with the minor axis of the first dilator and the minor axis of the second dilator is aligned with the major axis of the first dilator.

18 Claims, 11 Drawing Sheets

(56) References Cited

U.S. PATENT DOCUMENTS

| | | | |
|---|---|---|---|
| 2004/0059339 A1* | 3/2004 | Roehm, III | A61B 17/1757 606/90 |
| 2006/0030756 A1* | 2/2006 | Usher | A61B 17/00008 600/210 |
| 2006/0089536 A1* | 4/2006 | Perez-Cruet | A61B 17/02 600/210 |
| 2007/0270642 A1* | 11/2007 | Bayer | A61B 1/0005 600/109 |
| 2009/0221961 A1* | 9/2009 | Tal | A61M 25/0606 604/103.06 |
| 2010/0016757 A1* | 1/2010 | Greenburg | A61B 1/0125 600/562 |
| 2010/0114147 A1* | 5/2010 | Biyani | A61B 1/32 606/191 |
| 2010/0217090 A1* | 8/2010 | Heiges | A61B 17/02 600/217 |
| 2011/0118603 A1* | 5/2011 | Suh | A61B 5/4893 600/443 |
| 2011/0208226 A1* | 8/2011 | Fatone | A61B 17/3421 606/191 |
| 2011/0251461 A1* | 10/2011 | Gomez Gonzalez | A61B 17/3421 600/201 |
| 2011/0306835 A1* | 12/2011 | Chou | A61B 1/0051 600/113 |
| 2012/0004610 A1* | 1/2012 | Parker | A61B 25/0662 604/164.1 |
| 2013/0096603 A1* | 4/2013 | Mathis | A61B 1/2676 606/191 |
| 2013/0131718 A1* | 5/2013 | Jenson | A61B 17/0057 606/213 |
| 2013/0150793 A1* | 6/2013 | Beissel | A61M 25/0105 604/171 |
| 2013/0245382 A1* | 9/2013 | Simonson | A61B 17/025 600/210 |
| 2013/0345510 A1* | 12/2013 | Hadani | A61B 1/00183 600/113 |
| 2014/0031909 A1* | 1/2014 | Ye | A61N 1/0558 607/117 |
| 2014/0039264 A1* | 2/2014 | Heiman | A61B 17/025 600/202 |
| 2014/0128671 A1* | 5/2014 | Riek | A61B 1/00154 600/104 |
| 2014/0249562 A1* | 9/2014 | Root | A61M 29/00 606/191 |
| 2014/0277022 A1* | 9/2014 | Perrin | A61B 17/3209 606/167 |
| 2015/0025616 A1* | 1/2015 | Chang | A61B 17/12136 623/1.11 |
| 2015/0119920 A1* | 4/2015 | Mathis | A61B 17/12145 606/191 |
| 2015/0150497 A1* | 6/2015 | Goldchmit | A61B 8/12 600/439 |
| 2015/0216520 A1* | 8/2015 | Simonson | A61B 17/0218 600/204 |
| 2015/0230697 A1* | 8/2015 | Phee | A61B 1/0125 600/106 |

* cited by examiner

DILATION SYSTEM AND METHOD

BACKGROUND

1. Field of the Presently Disclosed Inventive Concepts

The inventive concepts disclosed and claimed herein relate to systems and methods for performing surgical procedures and, more particularly, but not by way of limitation, to systems and methods for accessing a surgical target site to perform surgical procedures.

2. Brief Description of Related Art

The present state of the art, when referencing a lateral surgical access approach, typically consists of using the following surgical instruments: neuromonitoring probe, dilators, and a retractor. Once an operative level is identified and an incision is created, dilators are used to create a surgical access site which is often followed by the use of a retractor or other specialized tools to create a surgical access corridor.

During a lateral approach to a patient's spine, a psoas muscle, which is located on either side of the spine, is separated in order to access the spine and, in particular, an intervertebral disc space or one or more vertebral bodies within a patient's spinal column. It is desirable to avoid neural elements or nerves of the lumbar plexus that lie within the psoas muscle during such procedures. The anterior third of the psoas muscle is typically considered a safe zone for muscle separation.

The neural elements or nerves of the psoas muscle may be mapped using a stimulating probe. In this manner, the most posterior neural or nerve-free area of the psoas muscle may be located and identified. The stimulating probe may then be inserted through the psoas muscle via the most posterior neural or nerve-free tissue area or through nearly any other region that is free of neural elements or nerves and toward the spine or into the intervertebral disc space in order to initiate safe tissue separation of the psoas muscle. Dilators are next placed over the probe to create and enlarge a surgical access site. Following the use of dilators, a retractor or other specialized tools are used to further enlarge the surgical access corridor.

Concentric dilators separate the muscle radially, and as such, dilate tissue on all both sides of the stimulating probe in a uniform fashion. This in turn may impinge on neural elements or nerves located outside of the safe zone. Directional dilators have been suggested to overcome the problems associated with concentric dilators. While directional dilation systems are effective for avoiding known neural elements, they are limited in their ability to continuously monitor nerve proximity and to create a surgical access site of a desired shape while at the same time reducing the amount of tissue damage.

BRIEF DESCRIPTION OF THE DRAWINGS

To assist those of ordinary skill in the relevant art in making and using the inventive concepts disclosed herein, reference is made to the appended drawings and schematics, which are not intended to be drawn to scale, and in which like reference numerals may refer to the same or similar elements for consistency. For purposes of clarity, not every component may be labeled in every drawing. Certain features and certain views of the figures may be shown exaggerated in scale or in schematic in the interest of clarity and conciseness. In the drawings.

DETAILED DESCRIPTION OF EXEMPLARY EMBODIMENTS

In the following detailed description of embodiments of the inventive concepts, numerous specific details are set forth in order to provide a more thorough understanding of the inventive concepts. However, it will be apparent to one of ordinary skill in the art that the inventive concepts disclosed and claimed herein may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a process, method, article, or apparatus that comprises a list of elements or steps is not necessarily limited to only those elements or steps and may include other elements, steps, or features not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Throughout this disclosure and the claims, the terms "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, or combinations thereof, for example.

The use of the term "at least one" will be understood to include one as well as any quantity more than one, including but not limited to each of, 2, 3, 4, 5, 10, 15, 20, 30, 40, 50, 100, and all integers therebetween. The term "at least one" may extend up to 100 or 1000 or more, depending on the term to which it is attached; in addition, the quantities of 100/1000 are not to be considered limiting, as higher limits may also produce satisfactory results. Singular terms shall include pluralities and plural terms shall include the singular unless indicated otherwise.

The term "or combinations thereof" as used herein refers to all permutations and/or combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment, although the inventive concepts disclosed herein are intended to encompass all combinations and permutations including one or more of the features of the embodiments described herein.

As generally understood by one of ordinary skill in the art, dilation systems will be described in detail herein in connection with accessing the spine or performing a surgical procedure, but dilation systems according to the inventive concepts disclosed herein may find use in any desired orthopaedic or other surgical procedures in which a surgeon wishes to gain access to an internal cavity by cutting the skin and going through the body wall in order to keep the incision spread apart so that surgical instruments can be inserted in the internal cavity. For example, dilation systems according to the inventive concepts disclosed herein may be used for anteriorly or posteriorly accessing the spine, for accessing the thoracic or cervical region of the spine, or for accessing any other part, cavity, or organ of the body of a human being or an animal.

Embodiments of dilation systems according to the inventive concepts disclosed herein may be used to gradually and atraumatically dilate a surgical opening by sequentially inserting two or more serial dilators into the surgical opening and rotating the dilators to enlarge the surgical opening. In some embodiments, the surgical opening may be enlarged by inserting a first dilator, rotating the first dilator, and inserting one or more second dilators over the first dilator, with each subsequent dilator being rotated to dilate the surgical opening. Further, in some embodiments dilations systems according to the inventive concepts disclosed herein may include reduced diameter dilators with standard or fixed-size stimulating probes.

Figure 1:
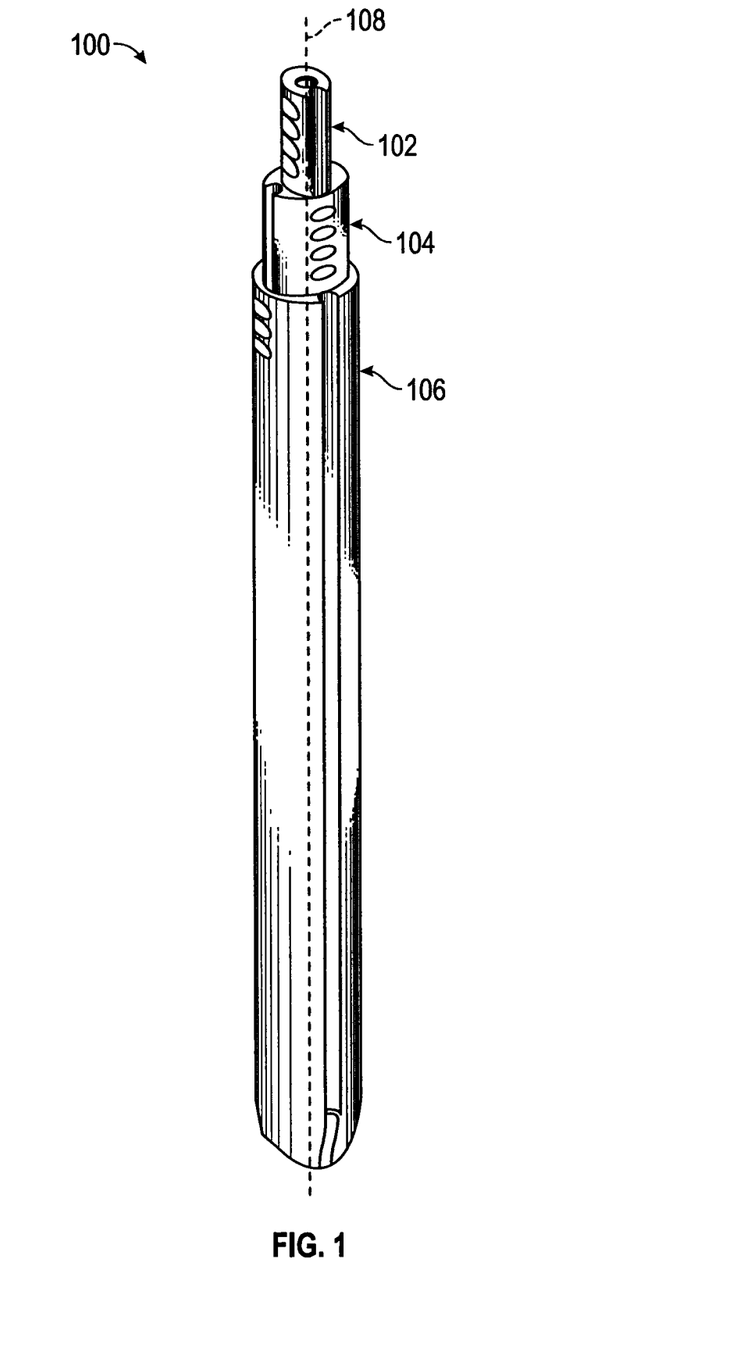
FIG. 1 is a perspective view of an embodiment of a dilation system constructed in accordance with the inventive concepts disclosed herein.
Figure 2:
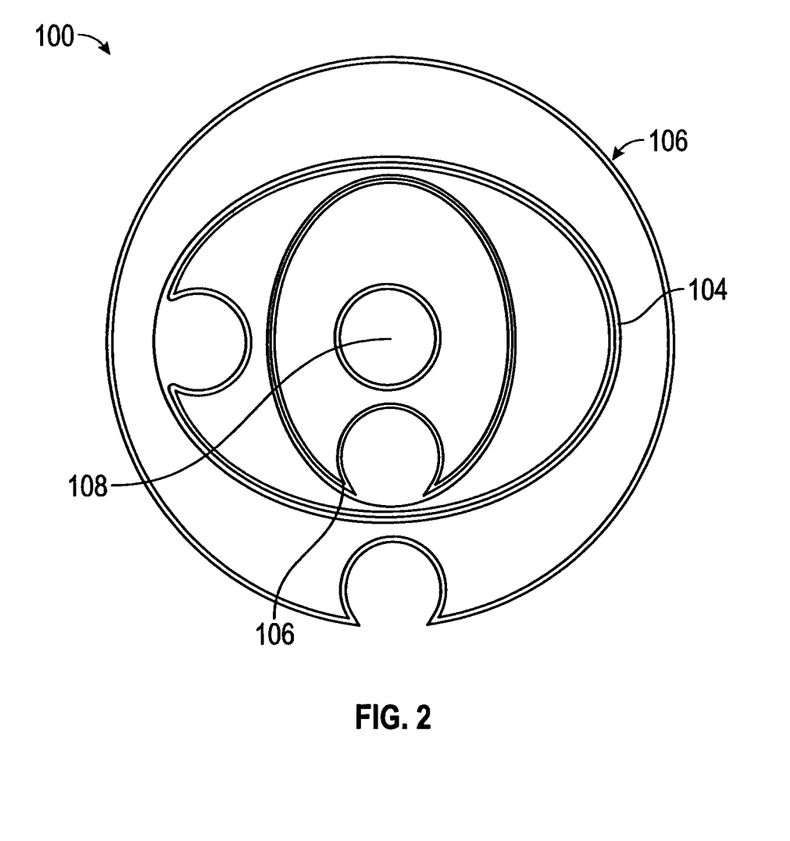
FIG. 2 is a top plan view of the dilation system of FIG. 1.

Referring to FIGS. 1-2, an embodiment of a dilation system 100 is illustrated. The dilation system 100 includes a first or initial dilator 102, one or more second or intermediate dilators 104, and a third or final dilator 106 configured to be matingly coupled with one another around a longitudinal axis 108. It is to be understood that dilation systems according to the inventive concepts disclosed herein may include any desired number of dilators, such as two, three, four, or more dilators. The dilation system 100 is configured to be used in combination with a monitoring K-wire or stimulating probe, such stimulating probe 170 depicted in FIG. 9A, for transmitting an electrical pulse as described below.

Figure 3:
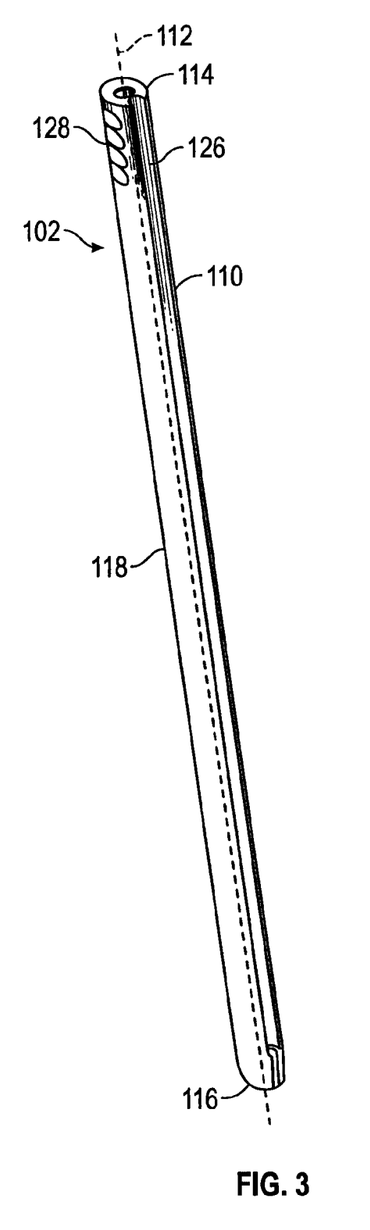
FIG. 3 is a perspective view of a first dilator constructed in accordance with the inventive concepts disclosed herein.
Figure 4:
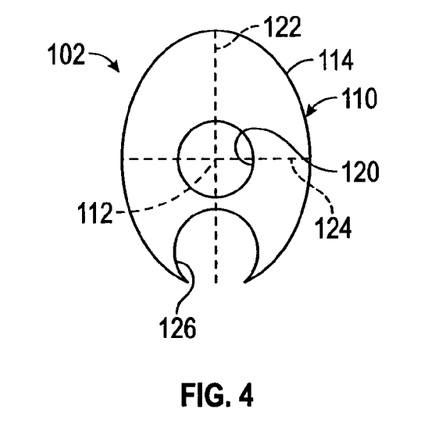
FIG. 4 is a top plan view of the first dilator of FIG. 3.

Referring now to FIGS. 3-4, the first dilator 102 includes an elongated body 110 having a longitudinal axis 112, a proximal end 114 a distal end 116, and an outer surface 118. The elongated body 110 may include a bore 120. The elongated body 110 has a substantially elliptical transverse cross-section and includes a major axis 122 and a minor axis 124 which are substantially normal to one another (e.g., substantially perpendicular to one another). The elongated body 110 has a first diameter (e.g., a transverse diameter) along the major axis 122 and a second diameter (e.g., a conjugate diameter) along the minor axis 124, with the first diameter being greater than the second diameter.

The outer surface 118 may include at least one channel 126 formed therein and extending along the outer surface 118 from the proximal end 114 to the distal end 116. The channel 126 is configured to slidably receive a stimulating probe, such as a stimulating probe 170a depicted in FIG. 9B). The channel 126 may extend along the outer surface 118 such that the channel 126 intersects the major axis 122 of the elongated body 110 in some embodiments. It is to be understood that in some embodiment the channel 126 may intersect the minor axis 124, may be tangental or positioned adjacent to the major axis 122 or the minor axis 124, and/or may be positioned so as not to intersect either the major axis 122 or the minor axis 124. Further, any number of channels 126 may be implemented with the first dilator 102 in some embodiments of the inventive concepts disclosed herein, such as two or more channels 126. In some embodiments where multiple channels 126 are implemented, one or more first channels 126 may intersect the major axis 122, and one or more second channels 126 may intersect the minor axis 124 as will be appreciated by persons of ordinary skill in the art having the benefit of the instant disclosure.

The outer surface 118 may taper inwardly adjacent to the distal end 116 so that the first dilator 102 is configured to minimize trauma to tissues when the distal end 116 of the first dilator 102 is inserted into a tissue. In some embodiments, the outer surface 118 may include a plurality of grasping notches 128 formed therein adjacent to the proximal end 114 of the elongated body 110. The grasping notches 128 may be configured to allow a surgeon to grip the first dilator 102 (e.g., manually or via a suitable surgical tool or robotic arm) and to manipulate the first dilator 102 as will be described below.

Referring again to FIG. 1, the elongated body 110 of the first dilator 102 is sized relative to the second dilator 104 such that a portion of the elongated body 110 (e.g., the proximal end 114 and/or a portion of the outer surface 118 including the grasping notches 128) remains accessible when the dilation system 100 is assembled and used as will be described below.

Figure 4A:
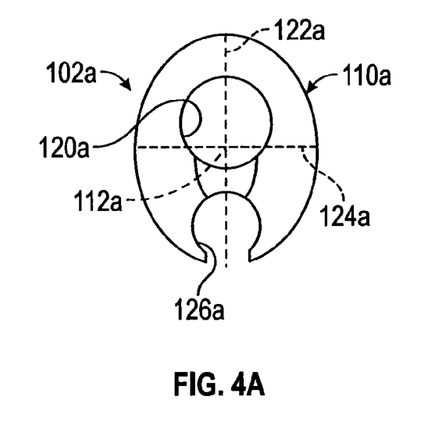
FIG. 4A is a top plan view of another embodiment of a first dilator constructed in accordance with the inventive concepts disclosed herein.

The bore 120 may extend through the elongated body 110 from the proximal end 114 to the distal end 116 and is configured to slidably receive a stimulating probe or a guide wire therein. In the embodiment shown in FIGS. 3-4, the bore 120 is substantially aligned with the longitudinal axis 112. However, in some embodiments, the bore 120 may be laterally offset from the longitudinal axis 112 or omitted. It is to be understood that while the bore 120 is shown as being substantially cylindrical in shape, the bore 120 may have any desired shape, size, and cross-section in some embodiments of the inventive concepts disclosed herein. For example, as shown in FIG. 4A, an embodiment of a first dilator 102a may be implemented similarly to the first dilator 102 and may include a bore 120a which is offset from the longitudinal axis 112a.

The first dilator 102 may be constructed of any desired material, such as stainless steel, surgical steel, titanium, metals, anodized aluminium, non-metals, polyether ether ketone (PEEK), polymers, resins, or combinations thereof, and may be constructed using any desired manufacturing technique, such as machining, casting, molding, or combinations thereof. In some embodiments, the first dilator 102 may be provided visual or haptic depth markings (e.g., along the outer surface 118) to indicate an appropriate insertion depth to a surgeon as will be appreciated by persons of ordinary skill in the art having the benefit of the instant disclosure.

Figure 5:
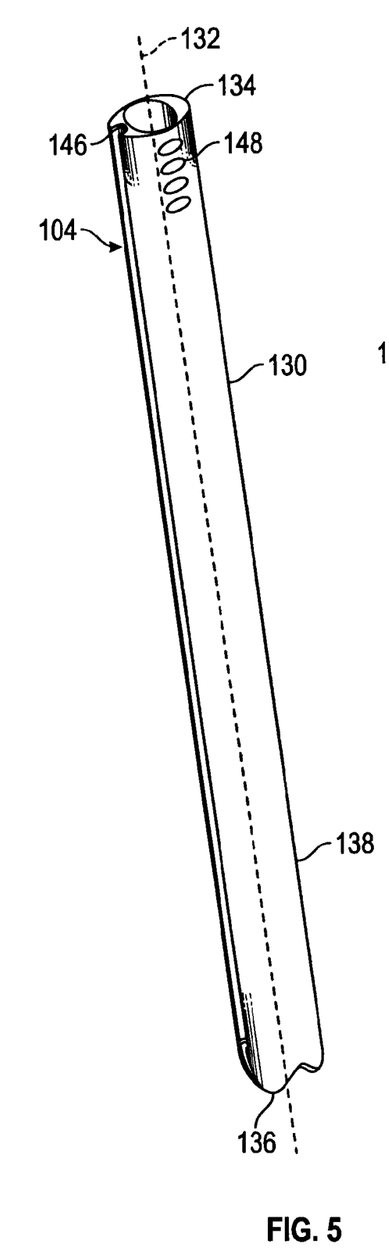
FIG. 5 is a perspective view of a second dilator constructed in accordance with the inventive concepts disclosed herein.
Figure 6:
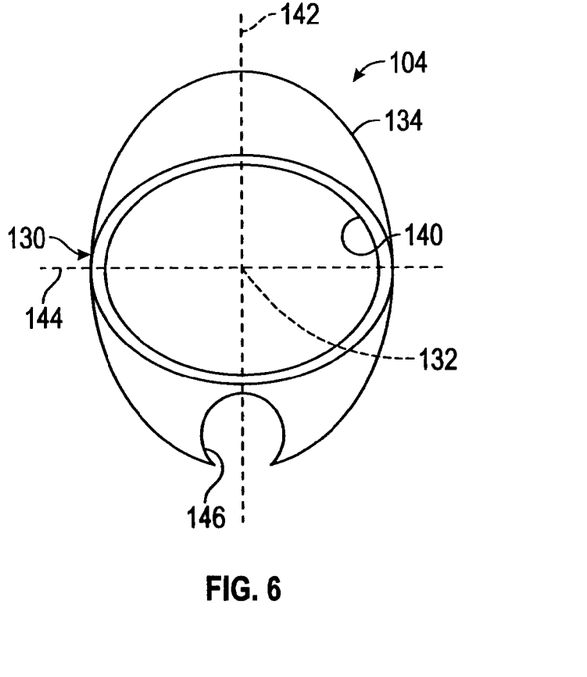
FIG. 6 is a top plan view of the second dilator of FIG. 5.

Referring now to FIGS. 5-6, the second dilator 104 may be implemented similarly to the first dilator 102 and includes an elongated body 130 having a longitudinal axis 132, a proximal end 134, a distal end 136, an outer surface 138 extending between the proximal end 134 and the distal end 136, and a bore 140 extending from the proximal end 134 to the distal end 136. The elongated body 130 has a substantially elliptical transverse cross-section and includes a major axis 142 and a minor axis 144 being substantially normal (e.g., substantially perpendicular) to the major axis 142. The elongated body 130 has a first diameter (e.g., a transverse diameter) along the major axis 142 and a second diameter (e.g., a conjugate diameter) along the minor axis 144, with the first diameter being greater than the second diameter.

The bore 140 is sized, shaped, and configured to matingly and slidably receive the first dilator 102 therein so that the major axis 142 of the second dilator 104 is aligned with the minor axis 124 of the first dilator 102 and the minor axis 144 of the second dilator 104 is aligned with the major axis 122 of the first dilator 102.

The outer surface 138 has at least one channel 146 for receiving a stimulating probe, the channel 146 extending from the proximal end 134 to the distal end 136 and intersecting the major axis 142 of the elongated body 130. It is to be understood that in some embodiments, the channel 146 may intersect the minor axis 144, may be tangental or positioned adjacent to the major axis 142 or the minor axis 144, and/or may be positioned so as not to intersect either the major axis 142 or the minor axis 144. Further, any number of channels 146 may be implemented with the second dilator 104 in some embodiments of the inventive concepts disclosed herein, such as two or more channels 146. In some embodiments where multiple channels 146 are implemented, one or more channel 146 may intersect the major axis 142, and one or more channel 146 may intersect the minor axis 144 as will be appreciated by persons of ordinary skill in the art having the benefit of the instant disclosure.

The outer surface 138 may taper adjacent to the distal end 136 so as to facilitate insertion into tissue. The general shape of the first dilator 102 is atraumatic. In some embodiments, the outer surface 138 may include a plurality of grasping notches 148 formed therein adjacent to the proximal end 134 of the elongated body 130. The grasping notches 148 may be configured to allow a surgeon to grip the second dilator 104 (e.g., manually or via a suitable surgical tool) and to manipulate the second dilator 104 as will be described below.

Referring again to FIG. 1, the elongated body 130 of the second dilator 104 is sized relative to the third dilator 106, such that a portion of the elongated body 130 (e.g., the proximal end 134 and/or a portion of the outer surface 138 including the grasping notches 148) remains accessible when the dilation system 100 is assembled and used as will be described below.

As will be appreciated by persons of ordinary skill in the art having the benefit of the instant disclosure, any desired number of second or intermediate dilators 104 may be implemented with the dilation system 100, such as one, two, three, or more of the second dilators 104. For example, where multiple second dilators 104 are implemented with an embodiment of the dilation system 100, each successive second dilator 104 may have a bore 140 configured to matingly (e.g., slidably) receive a preceding second dilator 104 therein such that the major axis 142 of one of the preceding second dilator 104 is substantially aligned with a minor axis 144 of the successive second dilator 104 and the minor axis 144 of the preceding second dilator 104 is substantially aligned with the major axis 142 of the successive second dilator 104.

Figure 7:
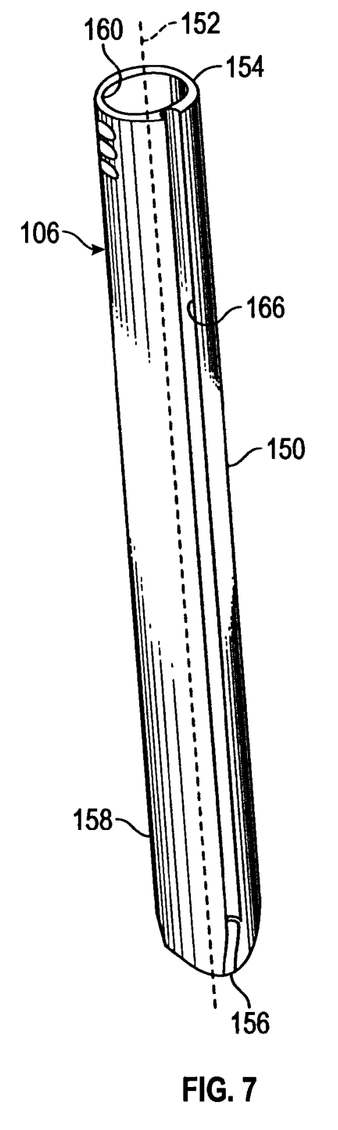
FIG. 7 is a perspective view of a third dilator constructed in accordance with the inventive concepts disclosed herein.
Figure 8:
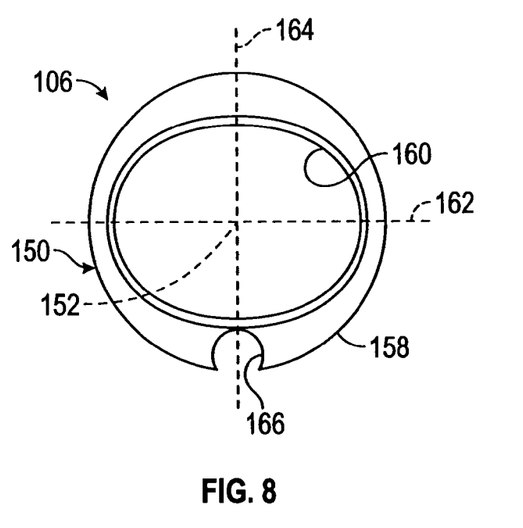
FIG. 8 is a top plan view of the third dilator of FIG. 7.

Referring now to FIGS. 7-8, the third dilator 106 may be implemented similarly to the first dilator 102 and includes an elongated body 150 having longitudinal axis 152, a proximal end 154, a distal end 156, an outer surface 158 extending between the proximal end 154 and the distal end 156, and a bore 160 extending from the proximal end 154 to the distal end 156. The elongated body 150 is illustrated as having a substantially circular transverse cross-section and is configured so as to allow the third dilator 106 to interface with a retractor, such as a multi-blade retractor in some embodiments.

The outer surface 158 may include at least one channel 166 for receiving a stimulating probe therein. The channel 166 may extend from the proximal end 154 to the distal end 156 and may be positioned so as to intersect the minor axis 144 of the elongated body 130 when the second dilator 104 is matingly received in the third dilator 106. It is to be understood that in some embodiment the channel 166 may be tangental or positioned adjacent to the major axis 142 and/or may be spaced a distance from the major axis 142. Further, any number of channels 166 may be implemented with the third dilator 106 in some embodiments of the inventive concepts disclosed herein, such as two or more channels 166.

The outer surface 158 may taper adjacent to the distal end 156 so as to facilitate insertion into tissue. The general shape of the second dilator 104 is atraumatic. In some embodiments, the outer surface 158 may include a plurality of grasping notches 159 formed therein adjacent to the proximal end 154 of the elongated body 150. The grasping notches 159 may be configured to allow a surgeon to grip the third dilator 106 (e.g., manually or via a suitable surgical tool) and to manipulate the third dilator 106 as described below.

The bore 160 has a substantially elliptical transverse cross-section and includes a major axis 162 and a minor axis 164, which may be substantially normal to one another. The bore 160 has a first diameter (e.g., a transverse diameter) along the major axis 162 and a second diameter (e.g., a conjugate diameter) along the minor axis 164, with the first diameter being greater than the second diameter. The bore 160 is configured to matingly and slidably receive the second dilator 104 therein such that the major axis 142 of the elongated body 130 is aligned with the major axis 162 of the bore 160 and such that the minor axis 144 of the elongated body 130 is aligned with the minor axis 164 of the bore 160.

As will be appreciated by persons of ordinary skill in the art having the benefit of the instant disclosure, in some embodiments the third dilator 106 may be omitted, while in some embodiments multiple third dilators 106 may be implemented, with each successive third dilator 106 having a bore 160 configured to matingly receive a preceding third dilator 106 therein.

Referring now to FIGS. 9A-9F, an exemplary embodiment of a method of using the dilation system 100 to access a lumbar region of a spine via a lateral approach will be described herein. However, a similar or the same method may be used with the dilation system 100 in other parts of a patient's body.

Figure 9A:
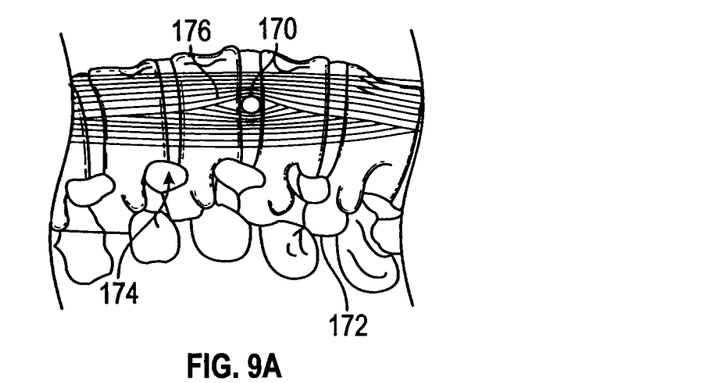
FIGS. 9A-9F illustrate a method of using the dilation system to dilate a surgical opening in a psoas muscle.

Using a stimulating probe 170 and an electromyograph (EMG) (not shown) in a manner similar to that described in U.S. Publication No. 2011/0208226, which is hereby expressly incorporated herein by reference in its entirety, a surgeon may map a safe zone (e.g., a zone generally free of neural elements or nerves) on a tissue of interest (e.g., psoas muscle). For example, on a human psoas muscle, the anterior third of the psoas muscle is generally considered a safe zone. Once a safe zone is established, anatomical placement may be confirmed via intra-operative fluoroscopy.

With a safe zone established, anatomical placement may be confirmed via intra-operative fluoroscopy. The surgeon inserts the stimulating probe 170 through the psoas muscle toward the patient's spine, as shown in FIG. 9A. If the surgery is being performed on the intervertebral disc space, the distal end of the stimulating probe 170 may be inserted into the annulus of the desired intervertebral disc space or may be positioned so that a tip of the stimulating probe 170 is proximate to the patient's spine 174. The stimulating probe 170 may be inserted via the most posterior portion of the safe zone in some embodiments.

Figure 9B:
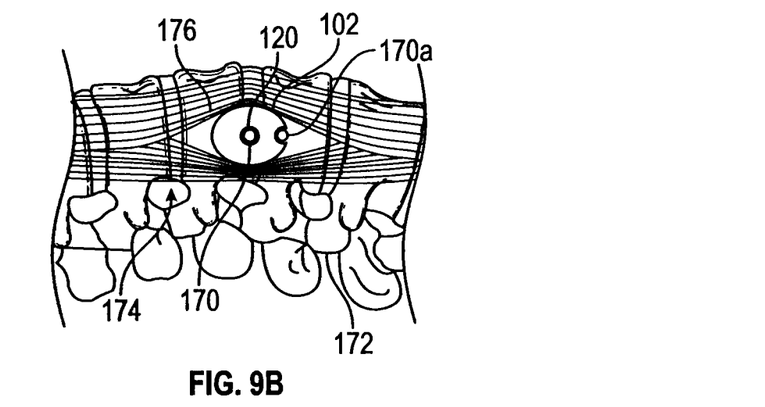

As shown in FIG. 9B, the surgeon may insert or slide the first dilator 102 over the stimulating probe 170 (e.g., such that the stimulating probe 170 is slidably received in the bore 120 of the first dilator 102) and may insert the distal end 116 and/or a portion of the elongated body 110 of the first dilator 102 through the psoas muscle 172 and toward the patient's spine 174. In some procedures, the first dilator 102 may be inserted through the psoas muscle without the use of a stimulating probe or guide wire. To minimize trauma to the psoas muscle 172 from the insertion of the first dilator 102 the first dilator 102 is inserted into the psoas muscle 172 such that the major axis 122 is oriented substantially parallel to the prevalent direction or orientation of psoas muscle fibers 176 adjacent to the insertion site and the minor axis 124 is oriented substantially perpendicular to the prevalent direction or orientation of psoas muscle fibers 176 adjacent to the insertion site. With the first dilator 102 inserted through the psoas muscle, an additional or secondary stimulating probe 170a may be inserted into the channel 126 to allow the surgeon determine the proximity of neural elements or nerves.

Figure 9C:
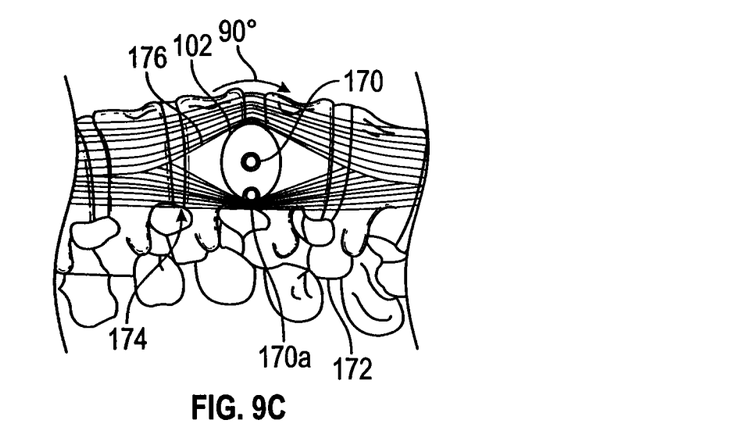

As shown in FIG. 9C, the surgeon may then rotate the first dilator 102 about the longitudinal axis 112 about 90° or about 270° (e.g., clockwise or counter clockwise) such that the major axis 122 is substantially perpendicular to the prevalent direction or orientation of psoas muscle fibers 176 adjacent to the insertion site and such that the minor axis 124 is substantially parallel to the prevalent direction or orientation of psoas muscle fibers 176 adjacent to the insertion site The stimulating probe 170a may be utilized before, during, and/or during rotating the first dilator 102 to transmit one or more electrical pulses via an EMG into the stimulating probe to determine the proximity of neural elements or nerves. For example, the first dilator 102 may be rotated so as to complete one or more rotations about the longitudinal axis 112 to enable the surgeon to locate a safe zone and/or determine the proximity of neural elements or nerves via the stimulating probe 170a. The insertion site is dilated or enlarged by the rotation of the first dilator 102 as a result of the major axis 122 of the first dilator 102 being greater than the minor axis 124 thereof. The stimulating probe 170a may be removed from the first dilator 102 after the first dilator 102 is rotated as described above.

Figure 9D:
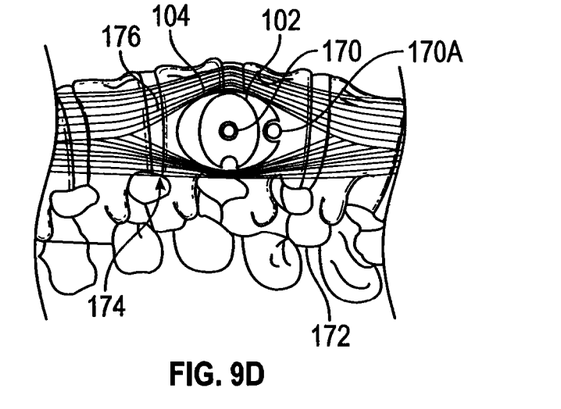

As shown in FIG. 9D, the surgeon can insert the second dilator 104 over the first dilator 102 and towards the patient's spine 174 by receiving the first dilator 102 in the bore 140 of the second dilator 104 in a way that the minor axis 144 of the second dilator 104 is aligned with the major axis 122 of the first dilator 102 the major axis 142 of the second dilator 104 is aligned with the minor axis 124 of the first dilator 102. This arrangement of the second dilator 104 relative to the first dilator 102 results in the distal end 136 of the second dilator 104 being initially inserted into the psoas muscle 172 so that the minor axis 144 of the second dilator 104 is oriented substantially perpendicular to the prevalent direction or orientation of psoas muscle fibers 176 adjacent to the insertion site and the major axis 142 is substantially parallel to the prevalent direction or orientation of psoas muscle fibers 176. With the second dilator 104 inserted through the psoas muscle 172, the stimulating probe 170a may be inserted into the channel 146 to allow the surgeon to determine the proximity of neural elements or nerves.

Figure 9E:
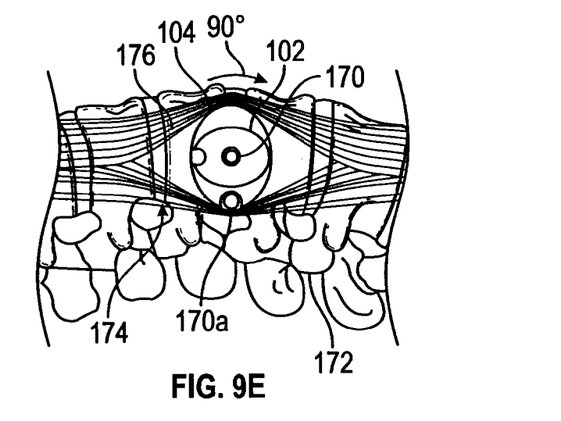

As shown in FIG. 9E, the surgeon may rotate the second dilator 104 about the longitudinal axis 132 about 90° or about 270° (e.g., clockwise or counter clockwise) such that the major axis 142 is substantially perpendicular to the prevalent direction or orientation of psoas muscle fibers 176 adjacent to the insertion site and such that the minor axis 144 is substantially parallel to the prevalent direction or orientation of psoas muscle fibers 176 adjacent to the insertion site. The stimulating probe 170a may be utilized before, during, and/or during rotating the second dilator 104 to transmit one or more electrical pulses via an EMG into the stimulating probe 170a to determine the proximity of neural elements or nerves. For example, the second dilator 104 may be rotated so as to complete one or more rotations about the longitudinal axis 132 to enable the surgeon to determine the proximity of neural elements or nerves via the stimulating probe 170a. The stimulating probe 170a may be removed after the second dilator 104 is rotated as described above.

The first dilator 102 is matingly received in the bore 140 of the second dilator 104 such that the second dilator 104 and the first dilator 102 move as a unit when the second dilator 104 is rotated. The insertion site is further dilated or enlarged by the rotation of the second dilator 104 as a result of the major axis 142 of the second dilator 104 being larger than the minor axis 144 of the second dilator 104.

The surgeon can insert one or more second or intermediate dilators 104 in a similar manner and rotating each successive second dilator 104 about 90° or about 270° (e.g., clockwise or counter clockwise) after insertion.

Figure 9F:
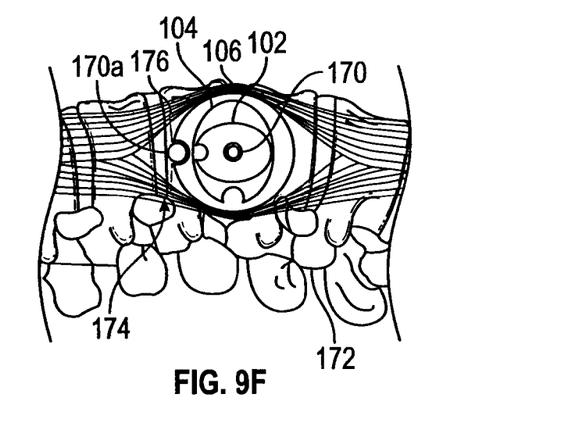
Figure 10:
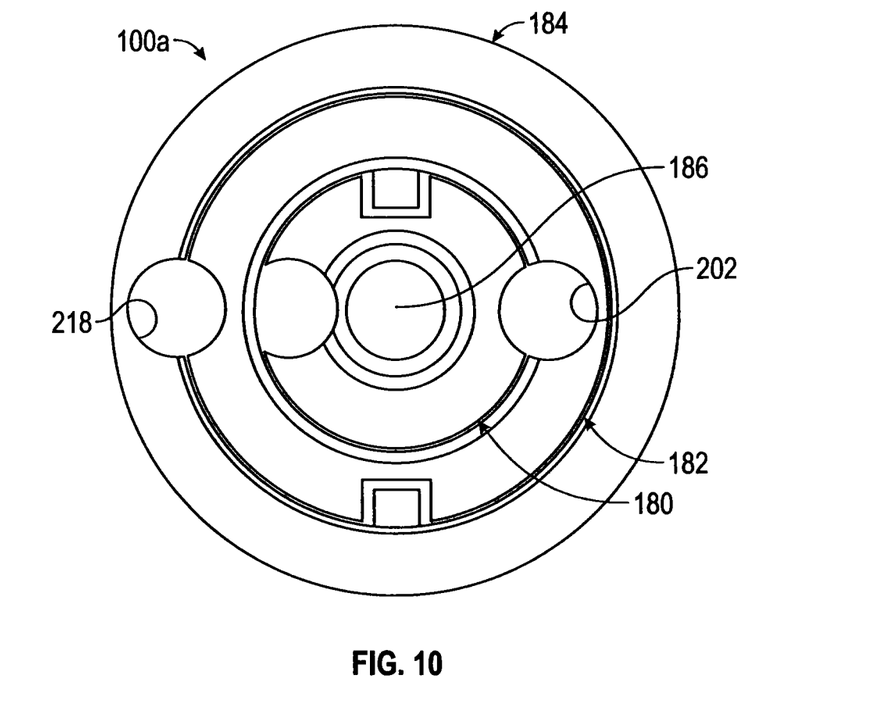
FIG. 10 is a top plan view of another embodiment of a dilation system constructed in accordance with the inventive concepts disclosed herein.

As shown in FIG. 9F, the surgeon can insert the third or final dilator 106 over the second dilator 104, for example, by slidably receiving the second dilator 104 in the bore 160 of the third dilator 106 such that the major axis 142 of the second dilator 104 is aligned with the major axis 162 of the bore 160 and the minor axis 144 is aligned with the minor axis 164 of the bore 160. The second dilator 104 is matingly received in the bore 160 of the third dilator 106 such that the third dilator 106 and the second dilator 104 move as a unit when the third dilator 106 is rotated. With the third dilator 106 inserted through the psoas muscle 172, the stimulating probe 170a may be inserted into the channel 166 to allow the surgeon to determine the proximity of neural elements or nerves by transmitting one or more electrical pulses via an EMG into the stimulating probe. For example, the surgeon may rotate the third dilator 106 between about 0° and about 360° (clockwise or counter clockwise) about the longitudinal axis 152 to enable the surgeon to determine the proximity of neural elements or nerves by transmitting one or more electrical pulses via an EMG into the stimulating probe 170*d*.

The third dilator 106 may interface with a retractor (not shown) that can be inserted over the third dilator 106 to subsequently retract the tissue and to permit removal of the dilation system 100 and the stimulating probes 170 and 170*a*.

As will be appreciated by persons of ordinary skill in the art, in some instances an external diameter of the dilators of dilation systems dictates the size of retractors that can be used with the particular dilation system. When the retractors have a relatively small diameter, generally smaller dilators are used to dilate the muscle prior to inserting the retractor. However, smaller diameter dilators may not have a sufficient thickness to accommodate a probe channel therein. This problem is especially relevant to the diameters of second and subsequent sequential dilators that are inserted over one another in a sequence. To address this issue, the first dilator may have an overall diameter configured to be as small as possible while still allowing the first dilator to accommodate a stimulating probe bore or channel therein. The second and subsequent dilators may be modified such that a portion of the respective stimulating probe channels extend into a bore for receiving the preceding dilator, thus resulting in a reduced overall diameter of each dilator and of the dilation system as a whole, while using a standard or fixed size stimulating probe.

Referring now to FIGS. 10-13, shown therein is an embodiment of a dilation system 100*a*. The dilation system 100*a* includes a first or initial dilator 180, a second or intermediate dilator 182, and a third or final dilator 184. The dilation system 100*a* may be configured to be used in combination with a monitoring K-wire or stimulating probe for transmitting an electrical pulse as described above.

Figure 11:
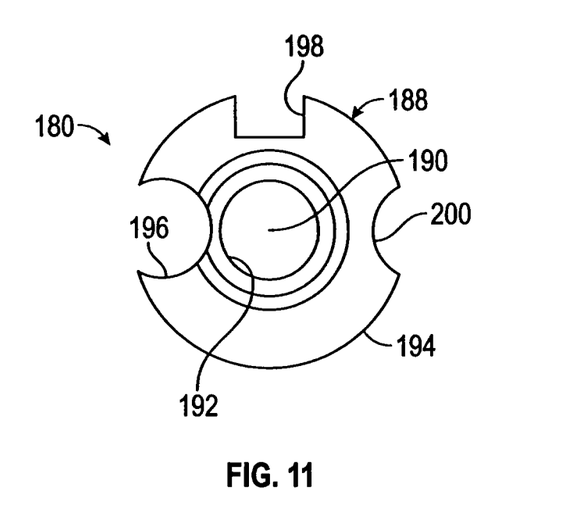
FIG. 11 is a top plan view of a first dilator of the dilation system of FIG. 10.

As shown in FIG. 11, the first dilator 180 includes an elongated body 188 having a longitudinal axis 190, a bore 192, and an outer surface 194. The elongated body 188 can be implemented similarly to the elongated body 110. The bore 192 may be implemented similarly to the bore 120 and is sized and configured to slidably receive a stimulating probe, such as the stimulating probe 170. In one embodiment, the bore 192 may be omitted from the elongated body 110.

The outer surface 194 has a substantially circular transverse cross-section but includes a channel 196, a keying slot 198, and a groove 200. The outer surface 194 may taper at a distal end of the elongated body 188 to facilitate insertion into tissue. The general shape of the first dilator 180 is atraumatic.

The channel 196 may be implemented similarly to the channel 126 and is configured to slidably receive a stimulating probe therein, such as the stimulating probe 170*a*. The keying slot 198 is configured to receive a keying pin therein so as to key the orientations of the first dilator 180 and the second dilator 182 relative to one another. It is to be understood that the keying slot 198 may have any desired shape, size, or cross-section and may be located adjacent to a proximal end of the elongated body 188 or may extend partially or substantially completely along the outer surface 194 of the elongated body 188 in some embodiments so as to not cause trauma to tissues or interfere with dilating a surgical opening during use of the first dilator 180.

The groove 200 is formed in the outer surface 194 and extends along the elongated body 188 such that the groove 200 may be aligned with a corresponding groove formed in the second dilator 182 as described below so as to form a combined lateral bore 202 (FIG. 10) for receiving a stimulating probe (e.g., the stimulating probe 170*a*). In some embodiments, the groove 200 is formed in the outer surface 194 so that the groove 200 is offset from the channel 196 at any desired distance or angle. In the embodiment shown in FIG. 11, the groove 200 is diametrically opposed to the channel 196 along the outer surface 194, however, in some embodiments the groove 200 may be adjacent to, tangental to, or positioned at any desired location along the outer surface 194 relative to the channel 196.

Figure 12:
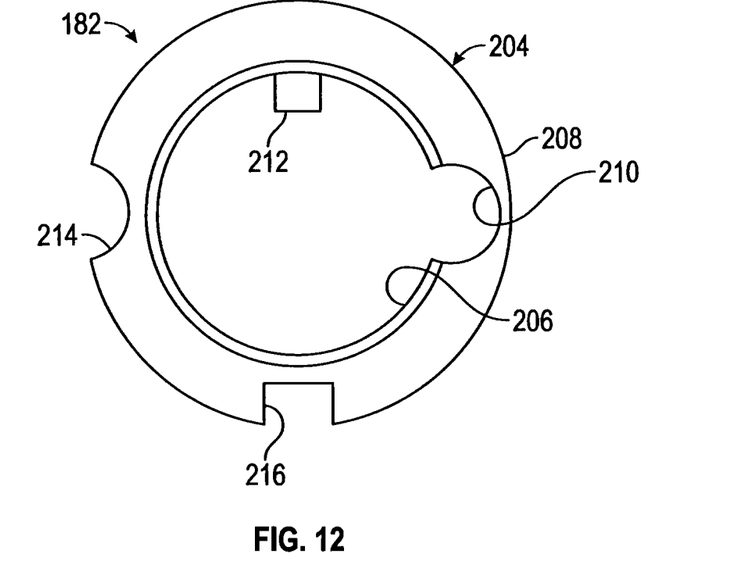
FIG. 12 is a top plan view of a second dilator of the dilation system of FIG. 10.

Referring now to FIG. 12, the second dilator 182 includes an elongated body 204 having a bore 206, and an outer surface 208. The bore 206 includes a groove 210 and a keying pin 212 formed therein and is sized, shaped, and configured to matingly and slidably receive the first dilator 180 therein so that the groove 210 aligns with the groove 200 of the first dilator 180 when the first dilator 180 is matingly received in the bore 206 such that the groove 210 and the groove 200 cooperate with one another to define the lateral bore 202 (FIG. 10) for receiving a stimulating probe, such as the stimulating probe 170*a*. As will be appreciated by persons of ordinary skill in the art having the benefit of the instant disclosure, the grooves 200 and 210 are configured so that when a stimulating probe, such as the stimulating probe 170*a* is inserted into the lateral bore 202, a portion of the stimulating probe 170 is received in the groove 200 and a portion of the stimulating probe 170 is received in the groove 210. By way of example, the diameter of the stimulating probe 170*a* may be about 3 mm, while the general thickness of the elongated body 206 may in a range from about 1 mm to about 3 mm.

The keying pin 212 is configured to be matingly received in the keying slot 198 such that the first dilator 180 is matingly received in the second dilator 182 so that the groove 210 aligns with the groove 200 to form the lateral bore 202.

The outer surface 208 includes a groove 214 and a keying slot 216. The outer surface 208 may be tapered at a distal end of the elongated body 204 to facilitate insertion into tissue. The general shape of the second dilator 182 is atraumatic.

The groove 214 may be implemented similarly to the groove 200 and extends along the elongated body 204, such that the groove 214 may be aligned with a corresponding groove formed in the third dilator 184 as described below so as to form a lateral bore 218 (FIG. 10) for receiving a stimulating probe therein. The groove 214 may be formed at any desired location in the outer surface 208. In some embodiments, the groove 214 may be positioned along the outer surface 208 so that the groove 214 aligns with the channel 196 when the first dilator 180 is matingly received by the second dilator 182.

The keying slot 216 may be implemented similarly to the keying slot 198 and is configured re receive a keying pin therein. The keying slot 216 may be positioned at any desired location and may be offset from the groove 214, the keying pin 212, and the groove 210 in some embodiments of the inventive concepts disclosed herein.

Figure 13:
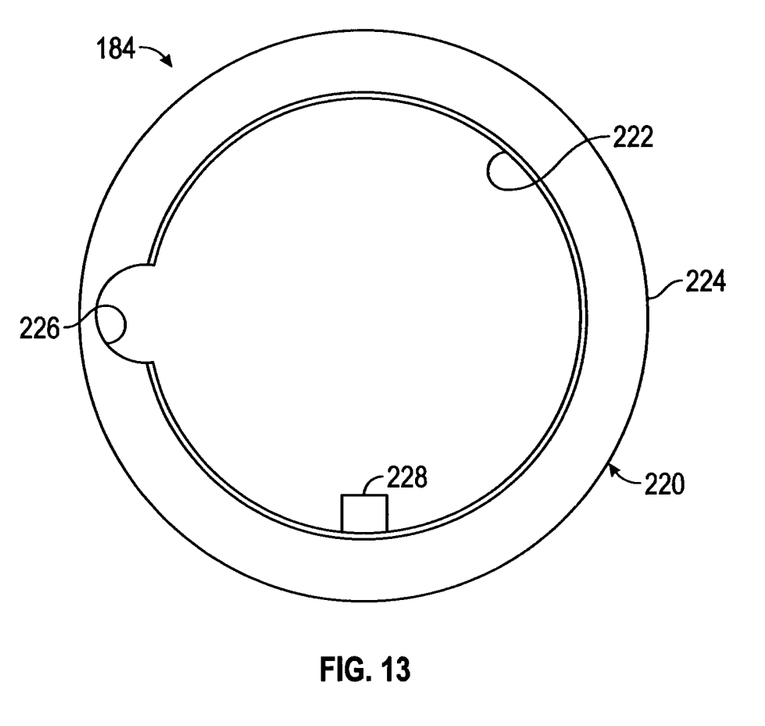
FIG. 13 is a top plan view of a third dilator of the dilation system of FIG. 10.
Figure 14:
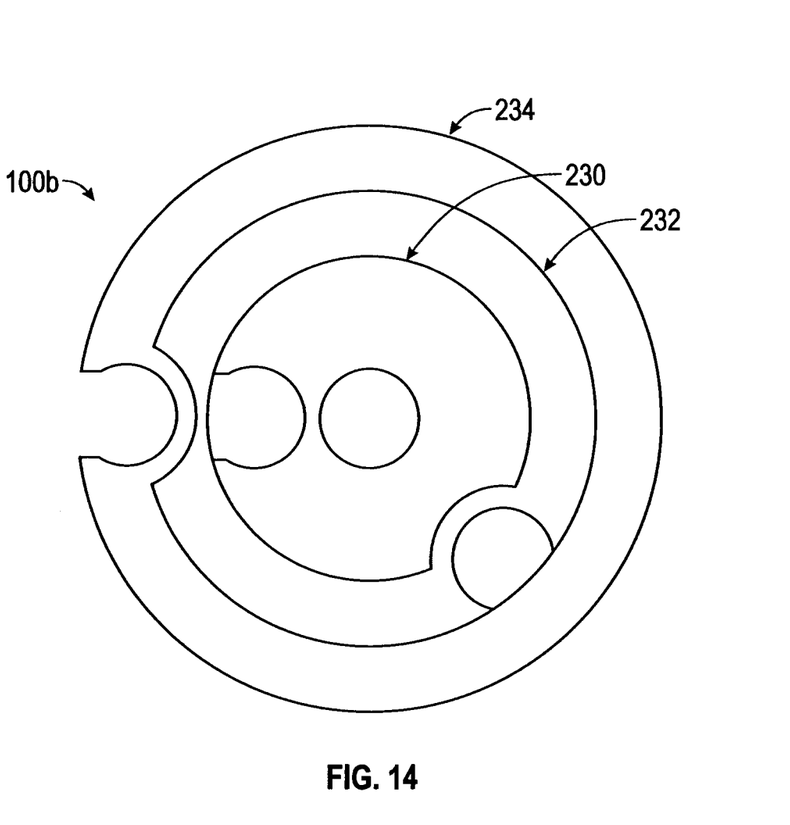
FIG. 14 is a top plan view of another embodiment of a dilation system constructed in accordance with the inventive concepts disclosed herein.

Referring now to FIG. 13, the third dilator 184 may be implemented similarly to the third dilator 106 and includes an elongated body 220 having a bore 222 and an outer surface 224. The bore 222 may be implemented similarly to the bore 206 and includes a groove 226 and a keying pin 228. The bore 222 is configured to matingly receive the second dilator 182 therein so that the groove 226 aligns with the groove 214 of the second dilator 182 when the second dilator 182 is matingly received in the bore 222 such that the groove 226 and the groove 214 cooperate with one another to define the lateral bore 218 (FIG. 10) for receiving a stimulating probe such as the stimulating probe 170 therein. By way of example, the diameter of the stimulating probe 170a may be about 3 mm, while the general thickness of the elongated body 220 may in a range from about 1 mm to about 3 mm.

Further, the keying pin 228 is matingly received in the keying slot 216 of the second dilator 182 so as to align the second dilator 182 and the third dilator 184 relative to one another as described above.

The outer surface 224 is configured so that the third dilator 184 interfaces with a retractor to subsequently retract the tissue and to permit removal of the dilation system 100a and the stimulating probes.

As will be appreciated by persons of ordinary skill in the art having the benefit of the instant disclosure, the dilation system 100a may be implemented with any number of dilators for example two, three, four, or more.

Referring now to FIGS. 14-17, shown therein is another embodiment of a dilation system 100b constructed in accordance with the inventive concepts disclosed herein. The dilation system 100b includes a first or initial dilator 230, a second or intermediate dilator 232, and a third or final dilator 234 configured to be matingly coupled with one another. The dilation system 100b is configured to be used in combination with a monitoring K-wire or stimulating probe, such as the stimulating probe 170, for transmitting an electrical pulse.

Figure 15:
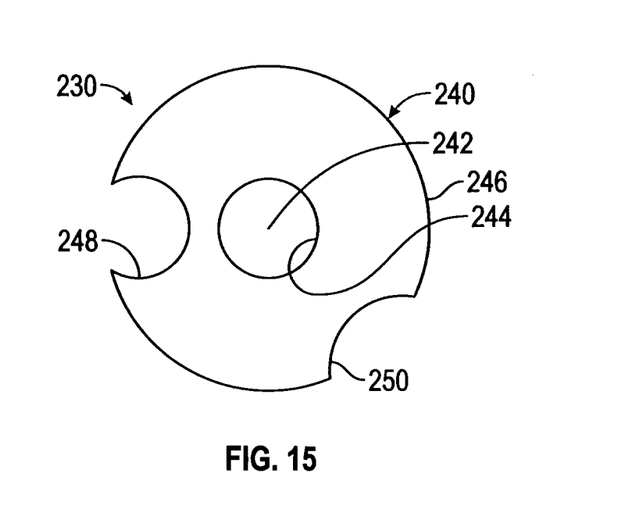
FIG. 15 is a top plan view of a first dilator of the dilation system of FIG. 14.

Referring now to FIG. 15, the first dilator 230 includes an elongated body 240 having a longitudinal axis 242, a bore 244, and an outer surface 246. The bore 244 may be implemented similarly to the bore 120 and is configured to slidably receive a stimulating probe such as the stimulating probe 170 therein.

The outer surface 246 includes a channel 248 and a groove 250. The channel 248 may be implemented similarly to the channel 126 and is configured to slidably receive a stimulating probe therein. The groove 250 may be implemented similarly to the groove 200 and is configured to receive a portion of the second dilator therein as described below.

Figure 16:
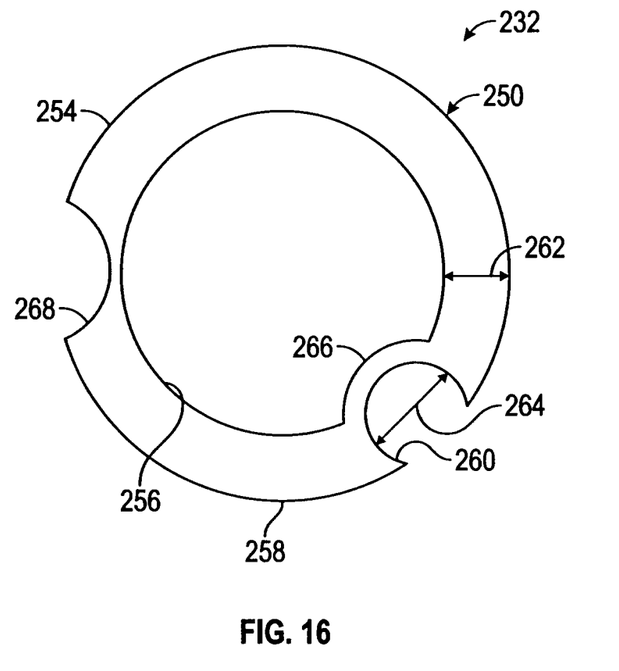
FIG. 16 is a top plan view of a second dilator of the dilation system of FIG. 14.

Referring now to FIG. 16, the second dilator 232 includes an elongated body 252 including a sidewall 254, a bore 256, an outer surface 258, and a channel 260. The sidewall 254 has a thickness 262. The bore 256 may be implemented similarly to the bore 206 and is configured to matingly receive the first dilator 230 therein.

The channel 260 is formed in sidewall 254 of the elongated body 252. In some embodiments, the channel 260 is sized and configured to receive a standard or fixed size stimulating probe, such as the stimulating probe 170a, and has a diameter 264 which is larger than the thickness 262 of the sidewall 254 such that a bridge portion 266 of the sidewall 254 extends inwardly into the bore 256. The bridge portion 266 is configured to be matingly received in the groove 250 when the second dilator 232 is positioned over the first dilator 230. By way of example, the diameter of the stimulating probe 170a may be about 3 mm, while the general thickness of the sidewall 254 of the elongated body 252 may in a range from about 1 mm to about 3 mm.

The outer surface 258 includes a groove 268. The groove 268 may be implemented similarly to the groove 250 and is configured to receive a portion of the third dilator 234 therein as described below. As will be appreciated by persons of ordinary skill in the art having the benefit of the instant disclosure, in some embodiments the groove 268 may be offset from the channel 260 along the outer surface 258 at any desired angle or distance.

Figure 17:
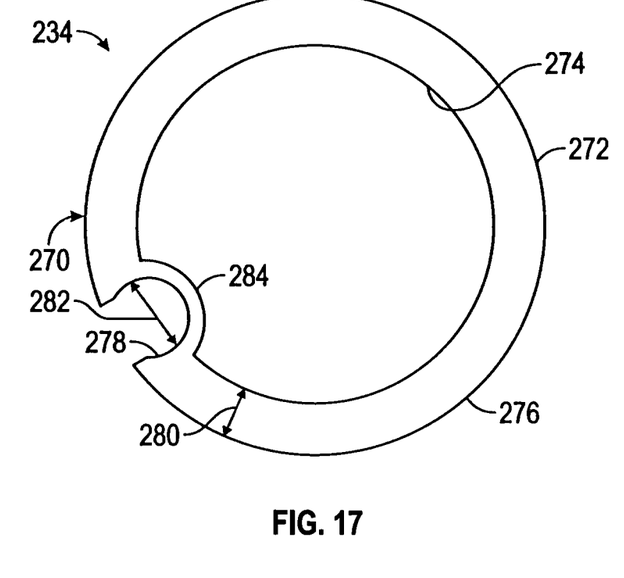
FIG. 17 is a top plan view of a third dilator of the dilation system of FIG. 14.

Referring now to FIG. 17, the third dilator 234 may be implemented similarly to the second dilator 232 and includes an elongated body 270 including a sidewall 272, a bore 274, an outer surface 276, and a channel 278. The elongated body 270 may be implemented similarly to the elongated body 252 described above. The sidewall 272 has a width 280. The bore 274 may be implemented similarly to the bore 256 and is configured to matingly receive the second dilator 232 therein. The channel 278 is formed in sidewall 272 of the elongated body 270 and is sized and configured so as to receive a standard or fixed size stimulating probe, such as the stimulating probe 170a. The channel 278 has a diameter 282 which is larger than the width 280 of the sidewall 272 such that a bridge portion 284 of the sidewall 272 extends inwardly into the bore 274. By way of example, the diameter of the stimulating probe 170a may be about 3 mm, while the general thickness of the sidewall 272 of the elongated body 270 may in a range from about 1 mm to about 3 mm. The bridge portion 284 is configured to be matingly received in the groove 268 when the second dilator 232 is matingly inserted into the bore 274. As will be appreciated by persons of ordinary skill in the art having the benefit of the instant disclosure, due to the groove 268 being offset from the channel 260 as described above, the channel 278 is offset from the channel 260.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

What is claimed is:

1. A dilation system, comprising:
   a first dilator including an elongated body having longitudinal axis, a proximal end, a distal end, and an outer surface extending between the proximal end and the distal end, the first dilator having a major axis and a minor axis, the minor axis being substantially normal to the major axis; and
   a second dilator including an elongated body having longitudinal axis, a proximal end, a distal end, an outer surface extending between the proximal end and the distal end, and a bore extending from the proximal end to the distal end, the second dilator having a major axis and a minor axis, the minor axis of the second dilator being substantially normal to the major axis of the second dilator, the bore of the second dilator configured to matingly receive the first dilator in such a way that the major axis of the second dilator is aligned with the minor axis of the first dilator and the minor axis of the second dilator is aligned with the major axis of the first dilator.

2. The dilation system of claim 1, wherein the elongated body of the first dilator has a bore extending from the proximal end to the distal end, and wherein the bore of the first dilator is aligned with the longitudinal axis of the first dilator.

3. The dilation system of claim 2, wherein the bore of the second dilator is aligned with the longitudinal axis of the second dilator.

4. The dilation system of claim 1, wherein the elongated body of the first dilator has a bore extending from the proximal end to the distal end, and wherein the bore of the first dilator is offset relative to the longitudinal axis of the first dilator.

5. The dilation system of claim 4, wherein the bore of the second dilator is aligned with the longitudinal axis of the second dilator.

6. The dilation system of claim 1, wherein the elongated body of the first dilator has at least one channel for receiving a stimulating probe, the channel extending from the proximal end to the distal end and intersecting the major axis of the first dilator.

7. The dilation system of claim 6, wherein the elongated body of the second dilator has at least one channel for receiving a stimulating probe, the channel extending from the proximal end to the distal end and intersecting the major axis of the second dilator.

8. The dilation system of claim 1 further comprising:
a third dilator including an elongated body having longitudinal axis, a proximal end, a distal end, an outer surface extending between the proximal end and the distal end, and a bore extending from the proximal end to the distal end, the third dilator having a substantially circular transverse cross section, the bore of the third dilator configured to matingly receive the second dilator.

9. The dilation system of claim 8, wherein the elongated body of the third dilator has at least one channel for receiving a stimulating probe, the channel extending from the proximal end to the distal end.

10. The dilation system of claim 1, wherein the bore of the second dilator is aligned with the longitudinal axis of the second dilator.

11. The dilation system of claim 1, wherein the elongated body of the second dilator has at least one channel for receiving a stimulating probe, the channel extending from the proximal end to the distal end and intersecting the major axis of the second dilator.

12. A method of forming an access opening through a psoas muscle to a patient's spine, the psoas muscle having a plurality of muscle fibers, the method comprising:
inserting a dilator having a major axis and a minor axis through the psoas muscle toward the patient's spine with the major axis of the dilator in a substantially parallel relationship to the muscle fibers of the psoas muscle; and
rotating the dilator to position the major axis of the dilator in a substantially perpendicular relationship to the muscle fibers of the psoas muscle.

13. The method of claim 12, wherein the dilator is a first dilator, and wherein the method further comprises:
inserting a second dilator having a major axis and a minor axis over the first dilator and through the psoas muscle toward the patient's spine with the major axis of the second dilator in a substantially parallel relationship to the muscle fibers of the psoas muscle; and
rotating the second dilator and the first dilator to position the major axis of the second dilator in a substantially perpendicular relationship to the muscle fibers of the psoas muscle.

14. The method of claim 13, further comprising:
inserting a third dilator having a circular transverse cross section over the second dilator and through the psoas muscle toward the patient's spine.

15. The method of claim 14, further comprising:
inserting a second stimulating probe into a channel extending from a proximal end to a distal end of the third dilator in a way to locate a safe zone in the psoas muscle.

16. The method of claim 13, further comprising:
inserting a stimulating probe into a channel extending from a proximal end to a distal end of the second dilator and intersecting the major axis of the second dilator in a way to locate a safe zone in the psoas muscle.

17. The method of claim 12 further comprising inserting a stimulating probe into the psoas muscle to locate a safe zone in the psoas muscle prior to inserting the dilator through the psoas muscle, and wherein the step of inserting the dilator further comprises inserting the dilator over the stimulating probe.

18. The method of claim 17, further comprising:
inserting a second stimulating probe into a channel extending from a proximal end to a distal end of the dilator and intersecting the major axis of the dilator in a way to locate a safe zone in the psoas muscle.

* * * * *